(12) United States Patent
Savara et al.

(10) Patent No.: US 12,600,690 B2
(45) Date of Patent: Apr. 14, 2026

(54) METHOD OF ETHANOL CONVERSION TO HIGHER CARBON COMPOUNDS

(71) Applicant: UT-Battelle, LLC, Oak Ridge, TN (US)

(72) Inventors: Aditya Savara, Oak Ridge, TN (US); Bo Chen, Oak Ridge, TN (US); Michelle K. Kidder, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 340 days.

(21) Appl. No.: 18/368,634

(22) Filed: Sep. 15, 2023

(65) Prior Publication Data

US 2024/0092715 A1    Mar. 21, 2024

Related U.S. Application Data

(60) Provisional application No. 63/407,190, filed on Sep. 16, 2022.

(51) Int. Cl.
| | |
|---|---|
| *C07C 45/29* | (2006.01) |
| *B01J 23/00* | (2006.01) |
| *B01J 23/02* | (2006.01) |
| *B01J 23/10* | (2006.01) |

(52) U.S. Cl.
CPC ............. *C07C 45/29* (2013.01); *B01J 23/002* (2013.01); *B01J 23/02* (2013.01); *B01J 23/10* (2013.01)

(58) Field of Classification Search
CPC .......... C07C 45/29; B01J 23/002; B01J 23/10
See application file for complete search history.

(56) References Cited

PUBLICATIONS

Rahman et al., "Effect of Water on Ethanol Conversion Over ZnO," Topics in Catalysis, 59(1), 37-45 (2016).
Chen et al., "Autothermal Reforming of Ethanol for Hydrogen Production Over Perovskite LaNiO3," Chemical Engineering Journal 160, 333-339 (2010).
Perin et al., "Manganese Based Perovskites in Ethanol Steam Reforming," Catalysis Letters 148, 220-226 (2018).
Song et al., "Ethanol Steam Reforming Over Co-Based Catalysts: Role of Oxygen Mobility," Journal of Catalysis 261, 66-74 (2009).
Natile et al., "La0.6Sr0.4Co1-yFeyO3-σ Perovskites: Influence of the Co/Fe Atomic Ratio on Properties and Catalytic Activity toward Alcohol Steam-Reforming," Chem. Mater. 20, 2314-2327 (2008).
Haryanto et al., "Current Status of Hydrogen Production Techniques by Steam Reforming of Ethanol: A Review," Energy and Fuels, 19, 2098-2106 (2005).
Llorca et al., "Direct Production of Hydrogen From Ethanolic Aqueous Solutions Over Oxide Catalysts," Chem. Commun., 641-642 (2001).

*Primary Examiner* — Sikarl A Witherspoon
(74) *Attorney, Agent, or Firm* — WARNER NORCROSS + JUDD LLP

(57) ABSTRACT

A method of ethanol conversion to higher carbon compounds is provided. The method includes feeding a reactant to a reactor, the reactant including ethanol. The reactant may further include water in the form of steam. The reactant is introduced to a perovskite catalyst in the reactor. The perovskite catalyst promotes the formation of the higher carbon compounds from ethanol, and may be in the form of a powder or thin film. The perovskite catalyst has the formula $ABO_3$, wherein A is one or more selected from a group consisting of La and Sr, and wherein B is one or more selected from a group consisting of Mn, Ca, Fe, and Co. The perovskite catalyst particularly may be $La_{0.7}Sr_{0.3}MnO_3$. The obtained higher carbon compounds may include at least one of acetone and crotonaldehyde.

18 Claims, 10 Drawing Sheets

| Molecule | Ethanol:Water = 1:0 | | Ethanol:Water = 1:9 | |
|---|---|---|---|---|
| | 673K | 773K | 673K | 773K |
| Ethanol | $(6.3 \pm 0.7) \times 10^{-3}$ | $(1.6 \pm 0.1) \times 10^{-3}$ | $(3.9 \pm 0.2) \times 10^{-3}$ | $(2.1 \pm 0.1) \times 10^{-3}$ |
| Acetone | $(0.1 \pm 0.5) \times 10^{-4}$ | $(0.1 \pm 0.3) \times 10^{-4}$ | $(1.5 \pm 0.2) \times 10^{-4}$ | $(2.0 \pm 0.3) \times 10^{-4}$ |
| Crotonaldehyde | $(1.1 \pm 3.2) \times 10^{-5}$ | $(0.0 \pm 3.7) \times 10^{-5}$ | $(0.0 \pm 1.6) \times 10^{-5}$ | $(0.0 \pm 2.7) \times 10^{-5}$ |
| Acetaldehyde | $(3.2 \pm 0.1) \times 10^{-2}$ | $(3.2 \pm 0.1) \times 10^{-2}$ | $(1.2 \pm 0.1) \times 10^{-2}$ | $(1.5 \pm 0.1) \times 10^{-2}$ |
| Ethene | $(1.3 \pm 0.1) \times 10^{-2}$ | $(1.4 \pm 0.1) \times 10^{-2}$ | $(0.3 \pm 0.1) \times 10^{-2}$ | $(0.4 \pm 0.1) \times 10^{-2}$ |
| Carbon Dioxide | $(0.0 \pm 0.8) \times 10^{-3}$ | $(0.0 \pm 0.8) \times 10^{-3}$ | $(8.6 \pm 0.4) \times 10^{-3}$ | $(9.5 \pm 0.5) \times 10^{-3}$ |
| Carbon Monoxide | $(0.0 \pm 0.4) \times 10^{-2}$ | $(0.4 \pm 0.2) \times 10^{-2}$ | $(5.4 \pm 0.2) \times 10^{-2}$ | $(4.8 \pm 0.2) \times 10^{-2}$ |
| Hydrogen | $(6.5 \pm 0.4) \times 10^{-2}$ | $(11.1 \pm 0.3) \times 10^{-2}$ | $(2.9 \pm 0.1) \times 10^{-2}$ | $(7.1 \pm 0.2) \times 10^{-2}$ |

FIG. 8

METHOD OF ETHANOL CONVERSION TO HIGHER CARBON COMPOUNDS

CROSS-REFERENCE TO RELATED APPLICATIONS

This application claims the benefit of U.S. Provisional Application No. 63/407,190, filed Sep. 16, 2022, the disclosure of which is incorporated by reference in its entirety.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

FIELD OF THE INVENTION

The present invention relates to a catalyst and method for converting ethanol to higher carbon compounds and other applications.

BACKGROUND OF THE INVENTION

Biomass-derived ethanol produced by fermentation or other processes is in abundant supply and readily available for use. The mechanisms for converting biomass-derived ethanol to commercially viable products are therefore of interest and as of yet not completely understood. One known process for conversion of ethanol is steam reforming in which ethanol and water are flown over a catalyst to produce products including $H_2$ and C2, C3, and C4 species. Conversion of ethanol (a two carbon (C2) molecule) into larger (three carbon (C3) or more) molecules is of particular industrial interest for the sustainable production of chemicals since ethanol is readily produced from certain plant-based biomass. It is desirable if such reactions can be conducted without any added oxidants or reductants, especially in the presence of water. Therefore, a need exists for such methods of converting ethanol to higher carbon compounds.

SUMMARY OF THE INVENTION

A method of ethanol conversion to higher carbon compounds is provided. The method includes feeding a reactant to a reactor. The reactant includes ethanol. The method further includes introducing the reactant to a perovskite catalyst in the reactor. The perovskite catalyst promotes the formation of the higher carbon compounds from ethanol.

In specific embodiments, the perovskite catalyst has the formula $ABO_3$, wherein A is one or more selected from a group consisting of La and Sr, and wherein B is one or more selected from a group consisting of Mn, Ca, Fe, and Co.

In specific embodiments, the perovskite catalyst is $La_{0.7}Sr_{0.3}MnO_3$.

In specific embodiments, the reactant further includes water.

In particular embodiments, the water is in the form of steam.

In other embodiments, the reactant does not include water.

In specific embodiments, the temperature in the reactor is in the range of 300 K to 800 K.

In specific embodiments, the pressure in the reactor is at atmospheric pressure.

In specific embodiments, the pressure in the reactor is below atmospheric pressure.

In specific embodiments, the perovskite catalyst is in the form of a powder or a thin film deposited on a crystal.

In specific embodiments, the higher carbon compounds include at least one of acetone and crotonaldehyde.

A method of producing acetone from ethanol is also provided. The method includes feeding a source of ethanol to a reactor, and feeding a source of water to the reactor. The method further includes introducing the ethanol and water to a catalyst including a perovskite in the reactor. The perovskite catalyzes a reaction of the ethanol in the presence of water to obtain acetone.

In specific embodiments, the perovskite is $La_{0.7}Sr_{0.3}MnO_3$.

In specific embodiments, the water is in the form of steam.

In specific embodiments, the ethanol is in the form of vapor.

In specific embodiments, the temperature in the reactor is in the range of 300 K to 800 K.

In specific embodiments, the pressure in the reactor is less than or equal to atmospheric pressure.

A catalyst for converting ethanol to higher carbon compounds is also provided. The catalyst includes a perovskite having the formula $ABO_3$, wherein A is one or more selected from a group consisting of La and Sr, and wherein B is one or more selected from a group consisting of Mn, Ca, Fe, and Co.

In specific embodiments, the perovskite is $La_{0.7}Sr_{0.3}MnO_3$.

These and other features of the invention will be more fully understood and appreciated by reference to the description of the embodiments and the drawings.

BRIEF DESCRIPTION OF THE DRAWINGS

FIG. 8 is a table of reaction product steady state partial pressures (in Torr) over $La_{0.7}Sr_{0.3}MnO_{3-x}(100)$ with continuous exposure of 0.1 Torr ethanol in the absence and presence of water;

US 12,600,690 B2

3

Figure 9:
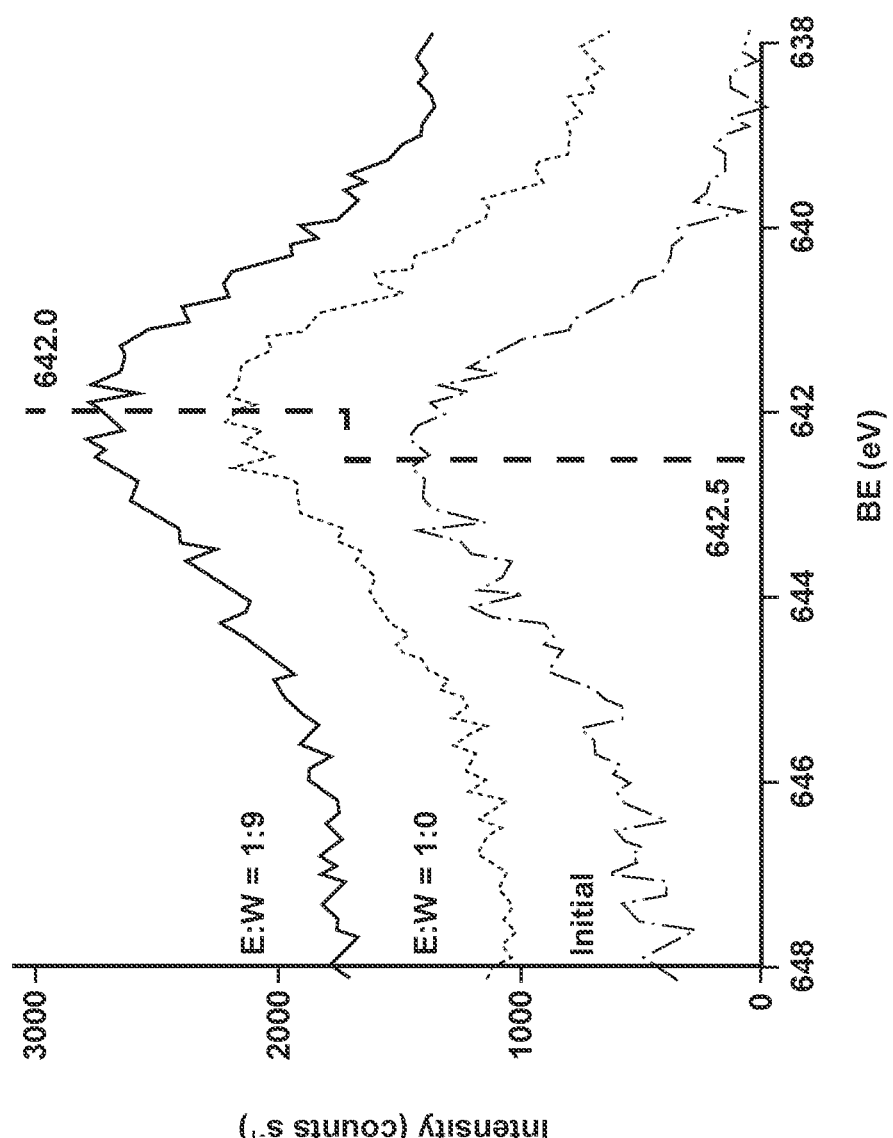
Figure 10:
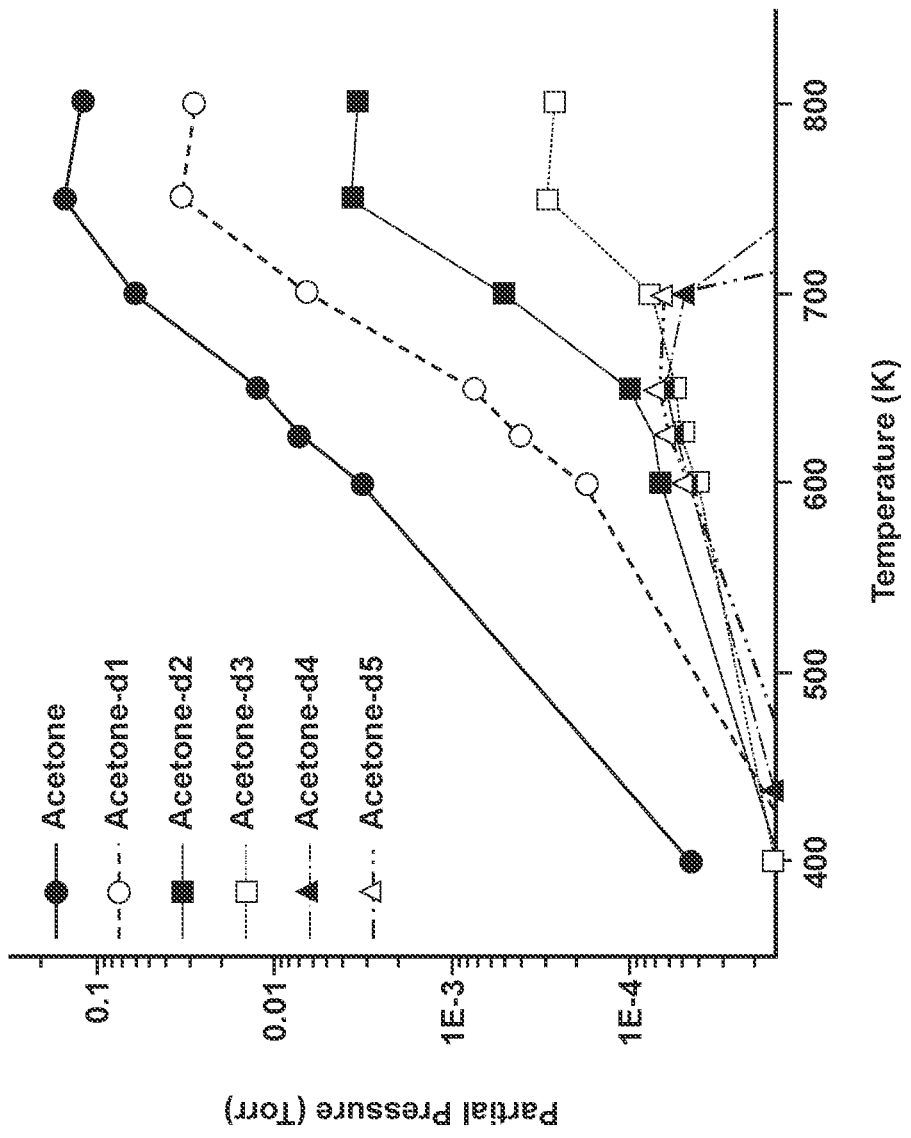
Figure 11:
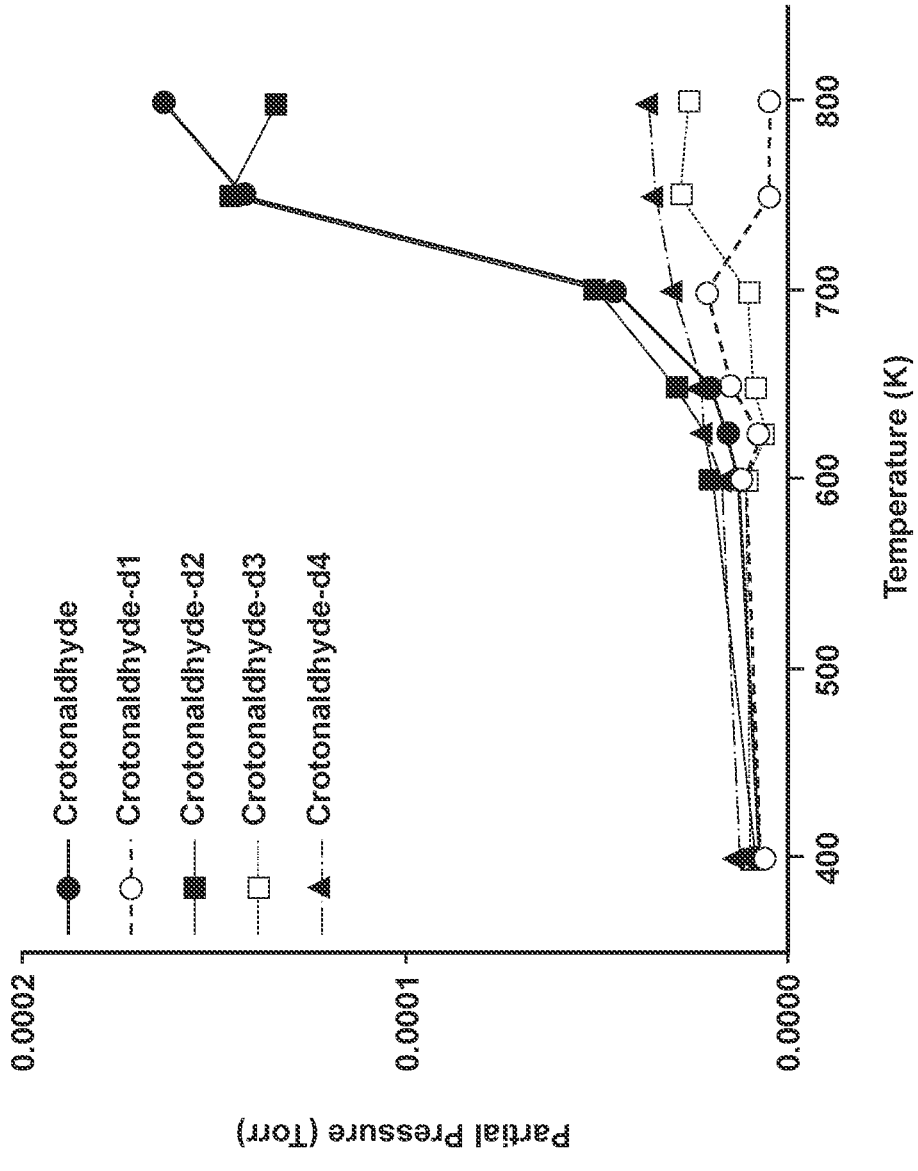
Figure 12:
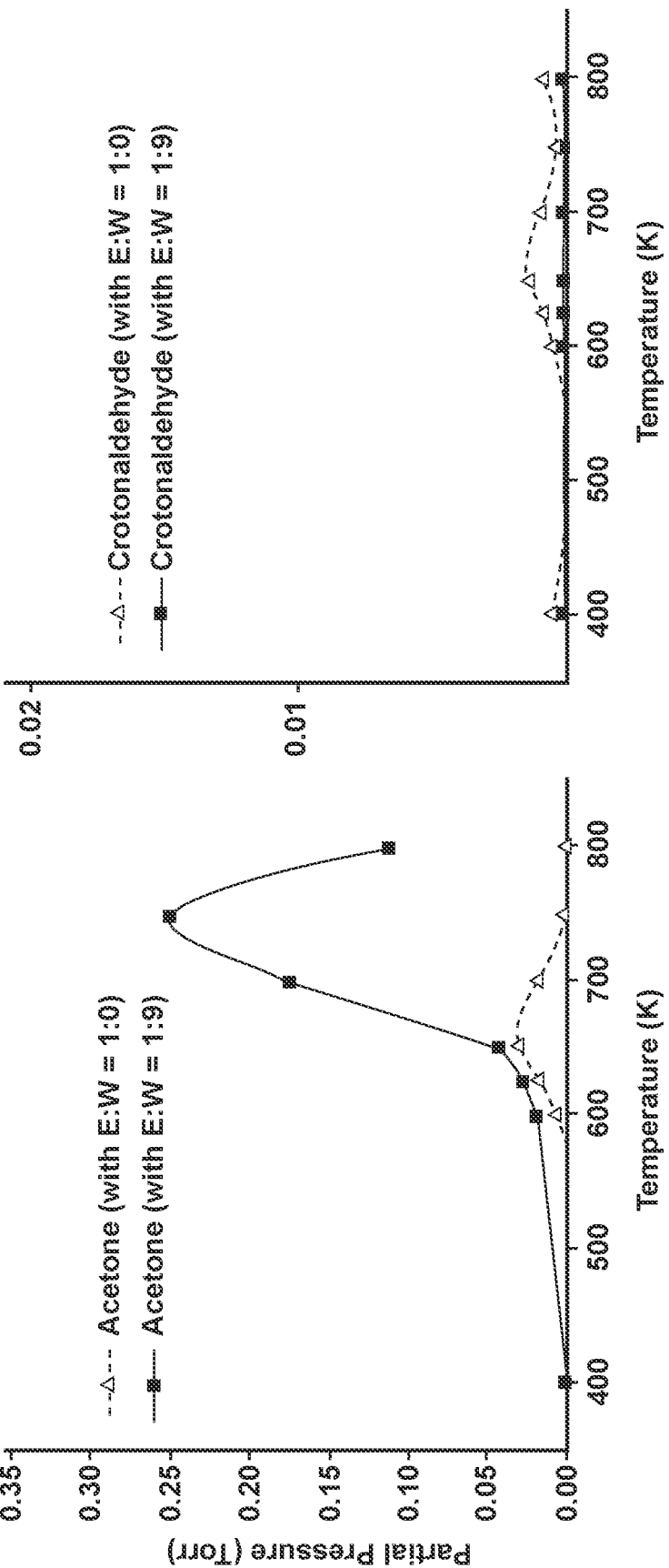
Figure 13:
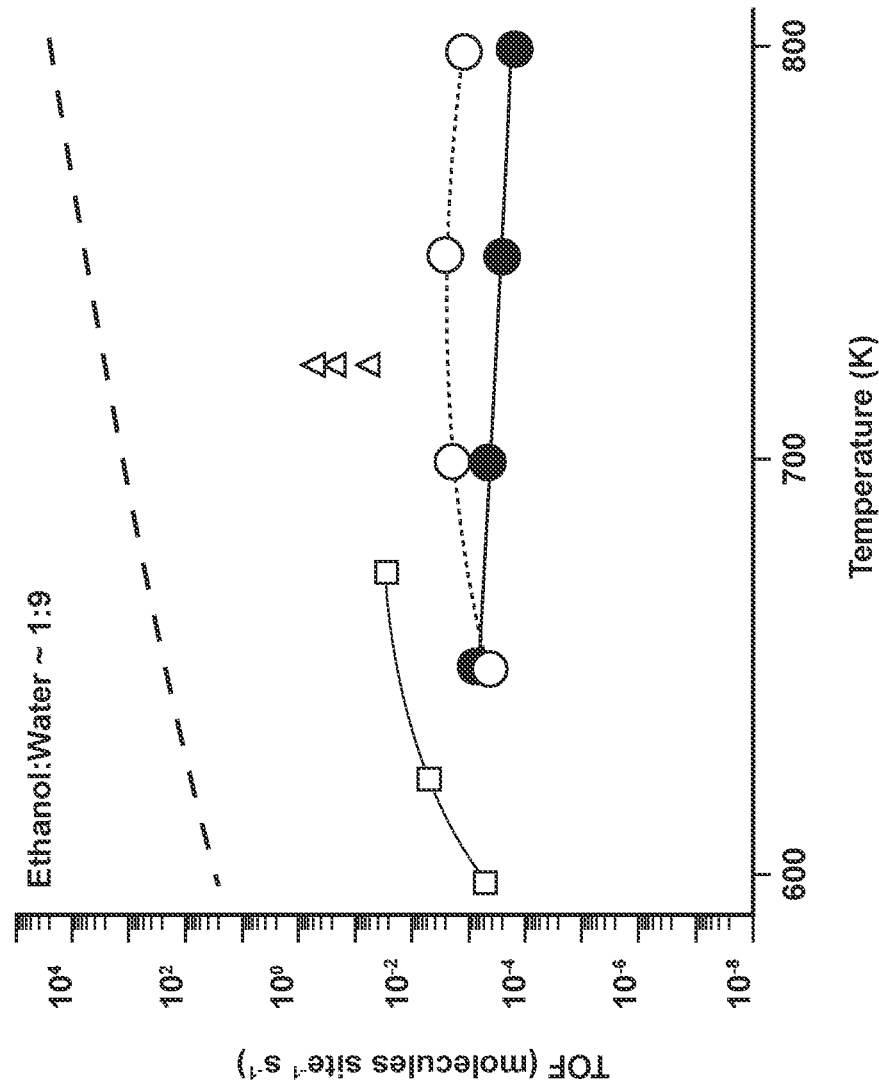

FIG. 9 is a graph of XPS Mn 2p 3/2 peak scan intensities versus binding energy obtained at 773 K under various conditions;

FIG. 10 is a graph of partial pressures of isotopically labelled acetone in the effluent for $CD_3CH_2OH$ conversion over $La_{0.7}Sr_{0.3}MnO_{3-x}$ powder with 1 Torr of $CD_3CH_2OH$ and 9 Torr of $H_2O$;

FIG. 11 is a graph of partial pressures of isotopically labelled crotonaldehyde in the effluent for $CD_3CH_2OH$ conversion over $La_{0.7}Sr_{0.3}MnO_{3-x}$ powder with 1 Torr of $CD_3CH_2OH$ and 9 Torr of $H_2O$;

FIG. 12 is graph of partial pressures of acetone and crotonaldehyde in the effluent for ethanol conversion over $La_{0.7}Sr_{0.3}MnO_3$ catalyst powder in the absence and presence of water; and FIG. 13 is a graph of turnover frequencies for acetone formation via ethanol conversion over $La_{0.7}Sr_{0.3}MnO_{3-x}$ powder and over a $La_{0.7}Sr_{0.3}MnO_{3-x}(100)$ single crystal in the presence of water in accordance with embodiments of the disclosure, as well as turnover frequencies for comparative examples.

DETAILED DESCRIPTION OF THE CURRENT EMBODIMENTS

As discussed herein, the current embodiments relate to a method of converting ethanol to higher carbon compounds including acetone and/or crotonaldehyde in the presence or absence of water, and a corresponding catalyst for the method. In one aspect, the method includes flowing ethanol over a perovskite catalyst. A mechanism of C—C coupling to achieve the C3 and C4 products of acetone and crotonaldehyde is also provided. Each step of the method and the mechanism is separately discussed below.

The method first includes feeding a reactant to a reactor. The reactant particularly includes ethanol, which may be obtained from any suitable source but advantageously may be ethanol produced from plant-based biomass. Further, the reactant(s) may or may not include water that is co-fed to the reactor from a water source. As such, the subsequent reaction may take place in the presence or absence of water. In some embodiments, the ethanol may be in the form of vapor/gas. Likewise, the water, if present, may be in the form of steam.

The method next includes introducing the reactant(s) to a perovskite catalyst in the reactor. Perovskite catalysts have a composition of $ABO_3$ where "A" and "B" are cations. In some embodiments, A is one or more of La and Sr, and B is one or more of Mn, Ca, Fe, and Co. In certain embodiments, the perovskite catalyst is specifically $La_{0.7}Sr_{0.3}MnO_3$. With such catalysts, particularly alkaline earth based perovskite catalysts, oxygen vacancies can occur on the surface under reaction conditions, and these chemical sites have the potential to bind the organic oxygenate reactants to facilitate coupling to create larger carbon chain products. Furthermore, the $ABO_3$ composition is tunable as both the A and B cations can be substituted. In the method, the perovskite catalysts may specifically be in the form of a powder such as in a powder bed. Alternatively, the perovskite catalysts may be in the form of a single crystal thin film.

The perovskite catalyst thus promotes the formation of the higher carbon compounds from ethanol. The higher carbon compounds include acetone and crotonaldehyde. Other products of the catalytic reaction may include one or more of hydrogen, carbon monoxide, carbon dioxide, ethene, and acetaldehyde.

The temperature in the reactor is not particularly limited, but in some embodiments may generally be in the range of 300 K to 800 K, optionally between 400 K and 800 K, optionally between 500 K and 800 K, optionally between 600 K and 800 K, or optionally between 700 K and 800 K. The pressure in the reactor is also not particularly limited, but is preferably at or below atmospheric pressure. In some embodiments, the pressure is generally at atmospheric pressure. In other embodiments, the pressure is below atmospheric pressure, such as under ultra high vacuum conditions. The base pressure of the reactor under ultra high vacuum conditions may be in the range of $1\times10^{-10}$ and $4\times10^{-10}$ Torr.

EXAMPLES

The present method is further described in connection with the following laboratory examples, which are intended to be non-limiting.

$La_{0.7}Sr_{0.3}MnO_3$ catalyst powders were synthesized by a solvothermal method, with the materials being purchased from Sigma Aldrich. Desired molar ratios of $La(NO_3)_3\cdot6H_2O$ (4.18 mmol), $Mn(NO_3)_2\cdot4H_2O$ (5.976 mmol), and $Sr(NO_3)_2$ (1.786 mmol) were placed in a Teflon bottle and dissolved with 30 mL of water while stirring. 6 mmol of citric acid was added and stirred for 1 hour at 40° C. Stirring was stopped and the mixture was heated to 100° C. for 24 hours, thereby forming a gel. The gel was heated to 500° C. at 10° C./minute in air and held at that temperature for 6 hours. The temperature was then ramped to 750° C. at 10° C./min and held at that temperature for 6 hours. Elemental analysis was then performed. The target elemental ratios were La (42.9%), Mn (24.3%), and Sr (11.7%). The measured elemental ratios were La (41.5%), Mn (23.1%), and Sr (11.6%). X-ray diffraction and scanning tunneling electron microscopy were also performed. Electron micrographs were collected on a scanning transmission electron microscopy (STEM, HD-2000, Hitachi, Japan) at 200 kV, and samples were loaded onto a 300 mesh copper grid with lacey carbon backing (Ted Pella, Inc). X-ray diffraction (XRD) patterns were collected on a PANalytical Empyrean powder diffractometer using CuK$\alpha$ radiation. The working voltage was 45 kV, and the current was 40 mA. The intensity data were collected at room temperature in the 2θ range of 10-90° with a step size of 0.026°.

The steady state kinetic measurements were performed on the $La_{0.7}Sr_{0.3}MnO_3$ catalyst powders in an Altamira Instruments system (AMI-200) using established procedures. The catalyst sample (10 mg, sieved to 180-400 μm) was diluted with quartz sand (177-250 μm) to minimize channeling and local temperature differences. The Brunauer-Emmett-Teller surface area was measured as 13.1 $m^2/g$ by $N_2$ adsorption. The quartz-to-catalyst mass ratio was approximately 10:1. The catalyst bed was placed inside a quartz U-tube and held in place by quartz wool at both ends of the bed. The sample was pretreated under 30 mL/min of 5% $O_2$ in Ar at approximately 800° C. for 5 hours. Liquid ethanol was fed into the system using a Chemyx Nexus 3000 syringe pump and He carrier gas with 30 mL/min flow rate and the system at atmospheric pressure. During the isothermal reaction experiments, the sample temperature was held at specified temperatures between 300 K and 800 K, with continuous exposure of ethanol. Products were analyzed using a ThermoStar Balzers GSD 300 mass spectrometer purchased from Pfeiffer. The MS sensitivity was calibrated employing ethanol as an internal standard.

$La_{0.7}Sr_{0.3}MnO_3(100)$ thin films with an average thickness of 20 nm were grown on 0.05% Nb-doped $SrTiO_3(100)$ crystal via pulsed laser deposition (PLD). Ultra-high vacuum surface chemistry experiments were performed in an ultra-high vacuum chamber. The base pressure of the chamber is typically between $1\times10^{-10}$ and $4\times10^{-10}$ Torr. Oxidized films were prepared under an oxygen partial pressure of $\sim1\times10^{-6}$ mbar at $\sim800$ K for $\sim2$ hours. Highly reduced surfaces were prepared with continuous ethanol exposure ($\sim5000$ L) at $\sim800$ K. The ethanol and water were introduced using a cylindrical-tube directed gas doser with a 50 µm diameter aperture. The sample was facing the doser with a small gap between the sample and doser ($\sim1$-2 mm) with the angle between the sample face and the mass spectrometer being $\sim90$ degrees. Two types of reaction experiments under continuous-exposure (CE) conditions were carried out to study quasi-steady state catalytic conversion over the surface. During the first type of experiment labeled CE-TPR, the sample surface was continuously exposed to ethanol and a temperature-programmed reaction (TPR) was performed with the sample temperature being ramped up from 300 K to 800 K at a rate of 1 K s$^{-1}$. During the second type of experiment called isothermal reaction, the sample temperature was held at certain temperatures between 300 K and 800 K, followed by continuous exposure of ethanol to react with the sample surface. Gas-phase reactants and reaction products were monitored using a Hiden HAL/3F 301 mass spectrometer.

The masses monitored during the experiments were 2, 18, 26, 27, 28, 29, 31, 32, 39, 41, 43, 44, 45, 46, 58, 60, 70, and 74 amu. This set of masses was chosen to identify key masses for molecules such as: 2 ($H_2$ and other molecules), 18 ($H_2O$), 26 (ethene), 27 (ethene), 28 (CO and other molecules), 29 (acetaldehyde), 31 (ethanol), 32 (glycolaldehyde), 39 (crotonaldehyde), 41 (crotonaldehyde), 43 (acetic acid and acetone), 44 ($CO_2$ and other molecules), 45 (acetic acid and ethanol), 46 (ethanol), 58 (acetone), 60 (acetic acid), 70 (crotonaldehyde), and 74 (diethyl ether). Reference patterns for these molecules were obtained from the NIST WebBook. These resolved signals were converted to resolved molecular concentrations based on correction factors determined using the method of Madix and Ko. The data was processed prior to analysis using Igor Pro 8 for background removal and peak deconvolution. The mass spectrometry data was analyzed with MSRESOLVE. Mass fragmentation patterns were obtained from NIST WebBook. The data was background subtracted and smoothed. Blank experiments were performed with only quartz sand (with no catalyst) as well as by considering the temperature of 400 K to be free from the catalysis of interest. The ethanol fragmentation pattern included masses associated with acetaldehyde and ethene. Additionally, ethanol can fragment inside a mass spectrometer to produce spurious signals of acetaldehyde and ethene. The data at 400 K was thus interpreted as not being from catalytic activity, and the higher temperature data was corrected accordingly. In MSRESOLVE, sequential linear subtraction with the feature for variance-based weighting for the subtraction order was used. The mass fragments that MSRESOLVE identified as indicative of each molecule were as follows: 70 (crotonaldehyde), 60 (acetic acid), 18 (water), 31 (ethanol), 2 ($H_2$), 58 (acetone), 29 (acetaldehyde), 26 (ethene), 44 (carbon dioxide), 28 (carbon monoxide), 16 (methane). No significant quantities of signals associated with methane, acetic acid, or 2-hydroxyethanal were observed. The mass fragmentation patterns overlap, and sequential linear subtraction accounted for this (for example, the mass 28 contribution associated with carbon monoxide is taken to be the signal remaining after all other molecular contributions have been subtracted). The final concentrations obtained had statistically constant carbon mass balance and were in semi-quantitative agreement with data from gas chromatography sampling collected for a separate study. The data was plotted (see below) with $1\sigma$ uncertainty intervals, that represented 68% confidence intervals, based upon the estimated experimental error, and assuming a 2% absolute intensity uncertainty in reference fragmentation patterns. The effluent carbon mass balance was within 95% confidence intervals of the feed during steady state flow experiments over powders.

Figures 1, 2:
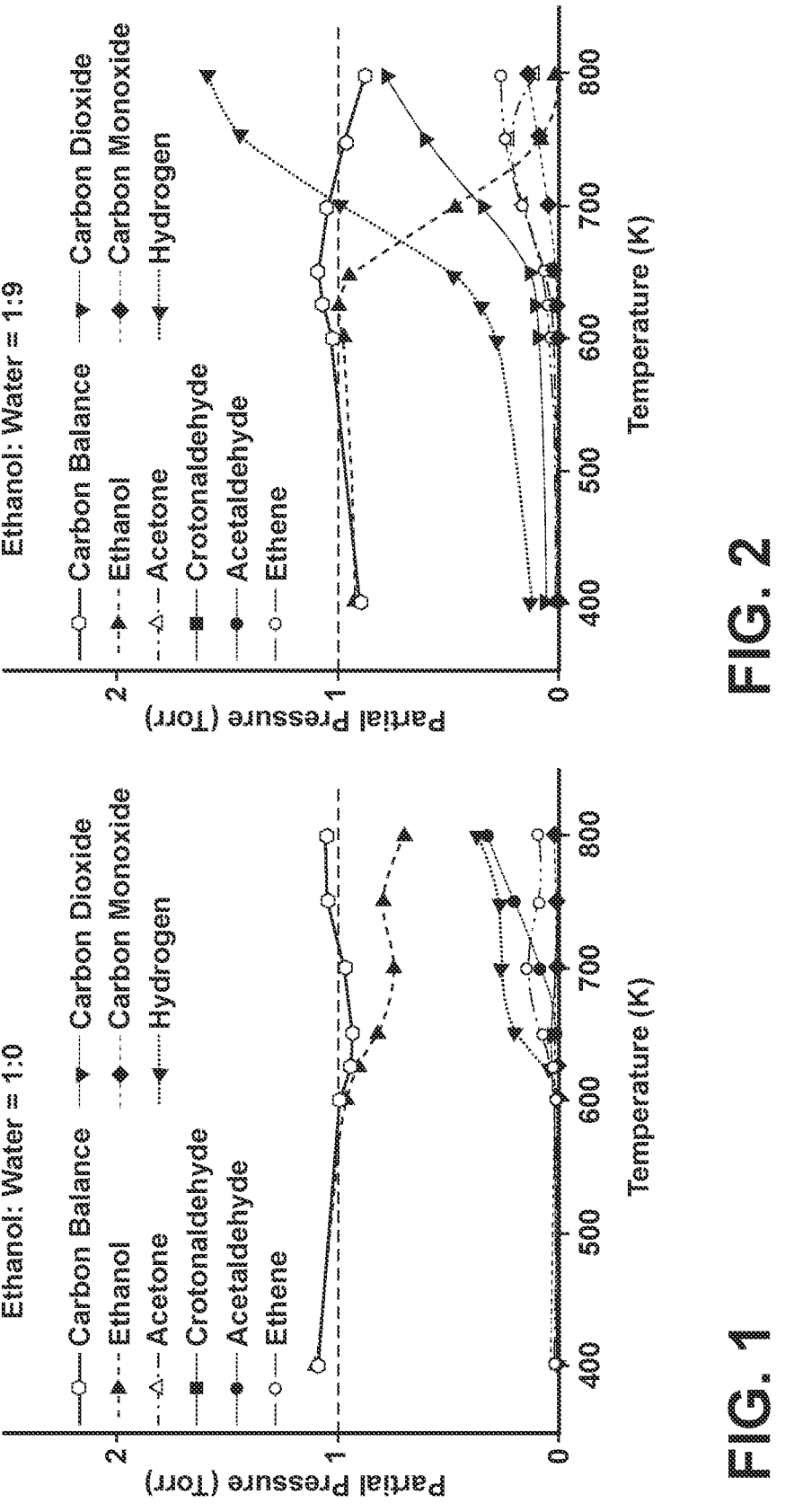
FIG. 1 is a graph of partial pressures of gases in the effluent for ethanol conversion over $La_{0.7}Sr_{0.3}MnO_3$ catalyst powder in the absence of water.
FIG. 2 is a graph of partial pressures of gases in the effluent for ethanol conversion over $La_{0.7}Sr_{0.3}MnO_3$ catalyst powder in the presence of excess water.
Figures 3, 4:
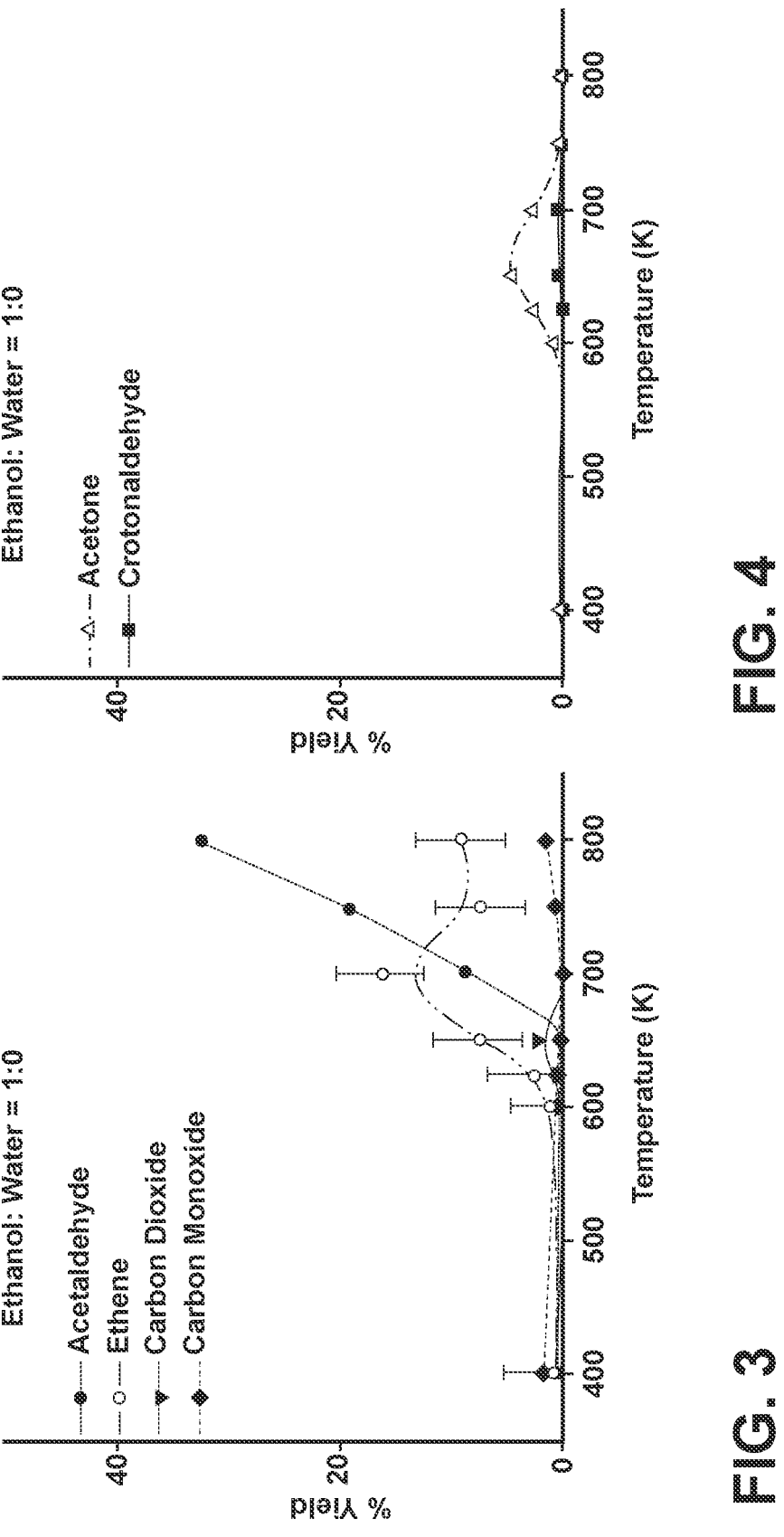
FIG. 3 is a graph of the percent yield of reaction products for ethanol conversion over $La_{0.7}Sr_{0.3}MnO_3$ catalyst powder in the absence of water.
FIG. 4 is a graph of the percent yield of other reaction products for ethanol conversion over $La_{0.7}Sr_{0.3}MnO_3$ catalyst powder in the absence of water.
Figures 5, 6:
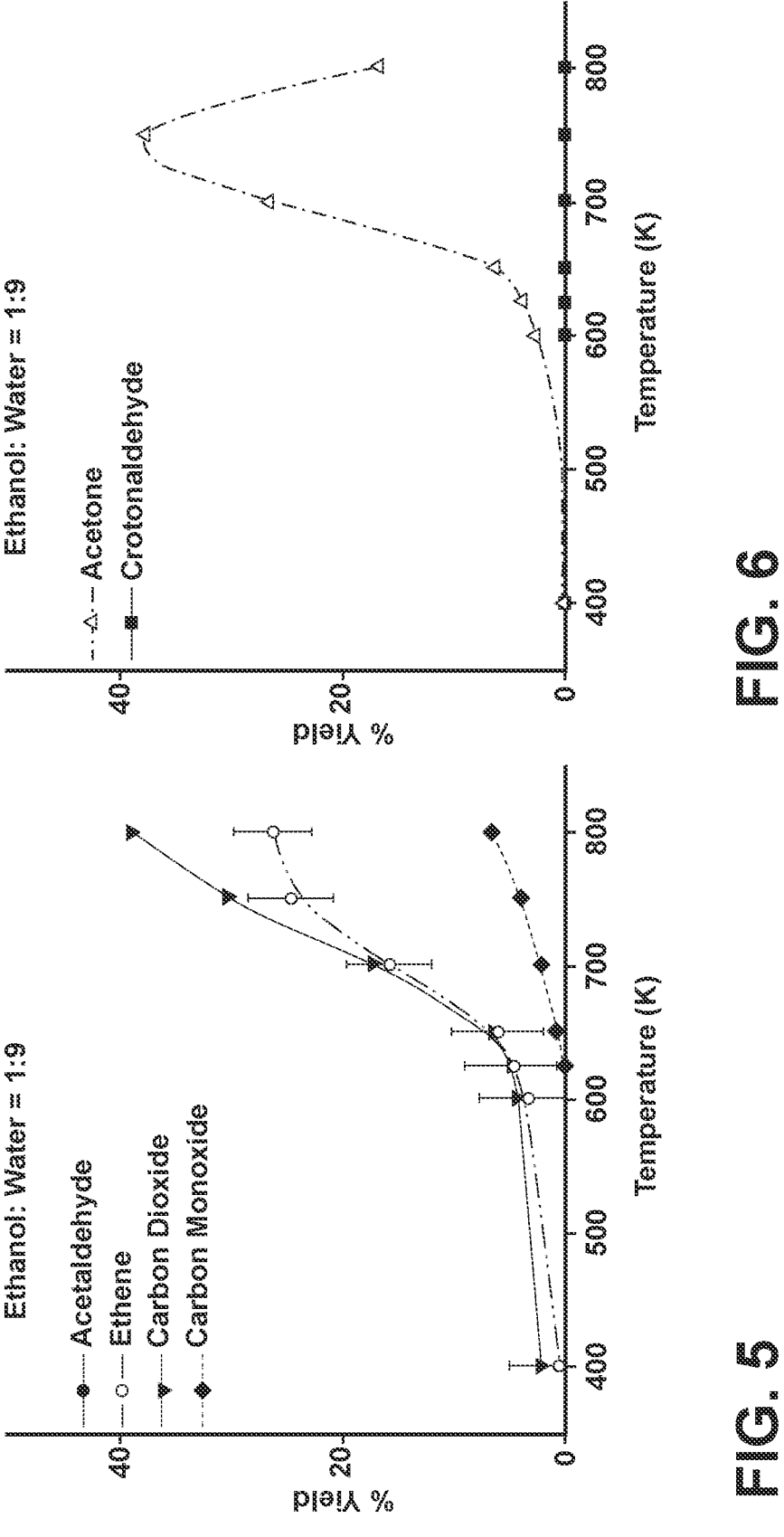
FIG. 5 is a graph of the percent yield of reaction products for ethanol conversion over $La_{0.7}Sr_{0.3}MnO_3$ catalyst powder in the presence of excess water.
FIG. 6 is a graph of the percent yield of other reaction products for ethanol conversion over $La_{0.7}Sr_{0.3}MnO_3$ catalyst powder in the presence of excess water.

To assess which product molecules were created and the trends as a function of reaction conditions, catalytic conversion of ethanol was studied in the absence of water and in the presence of an excess of water over $La_{0.7}Sr_{0.3}MnO_{3-x}$ powder from 400-800 K. In both cases, the partial pressure of ethanol in the feed was 1 Torr. For experiments with water in the feed to investigate the mechanism of steam reforming, the partial pressure of water in the feed was 9 Torr. At steady-state, the carbon balance in the effluent matched the quantity of the carbon in the feed within 95% confidence intervals. The steady state partial pressures of the gas phase products are shown as a function of temperature in FIG. 1 (absence of water) and FIG. 2 (with water), with the error bars representing $1\sigma$ uncertainties. To better understand the selectivity trends, the % yield, defined relative to total carbon, were plotted as shown in FIGS. 3-4 (absence of water) and FIGS. 5-6 (with water), with the error bars again representing $1\sigma$ uncertainties. It is evident that the quantity of acetone produced when a large excess of water is intentionally fed is much greater than the quantity of acetone produced when only ethanol is fed, i.e. when water is absent. The acetone produced in the presence of water is greater than the acetone produced in the absence of water for all temperatures, while the opposite is true for crotonaldehyde. Evidently, water promotes acetone in a way that either suppresses or takes away from the crotonaldehyde-producing pathway (further discussed below). Acetic acid was not detected in the effluent.

The $La_{0.7}Sr_{0.3}MnO_{3-x}$ powders are expected to be terminated by primarily (100) facets, based on thermodynamic considerations. Accordingly, the chemistry over single crystal samples with $La_{0.7}Sr_{0.3}MnO_{3-x}(100)$ termination was studied, which enabled the use of ultra high vacuum methods, such as x-ray photoelectron spectroscopy. These single crystal samples had faces of $\sim1$ cm×1 cm. By exposing the active face to a continuous exposure of the reactant gases (ethanol and water) while monitoring with mass spectrometry, the catalytic rates of product formation were obtained in molecules cm$^{-2}$ s$^{-1}$. Experiments were initially performed with an ethanol flux of $7.29\times10^{14}$ molecules cm$^{-2}$ s$^{-1}$ which is equivalent to a pressure of $3.25\times10^{-9}$ bar of ethanol. Catalytic activity was observed with ethene, acetaldehyde, CO, $CO_2$, $H_2O$, and $H_2$. It was observed that the presence of water significantly promotes combustion type pathways (to CO, $CO_2$, and $H_2O$), while also suppressing the acetaldehyde and ethene formation pathways. Recognizing that water is able to fill oxygen vacancies in the temperature range being studied, it can be rationalized that CO production increases by combustion type pathways when an oxygen source is available, and also that water can suppress the ethene and acetaldehyde production catalyzed by oxygen vacancies. Under this flux equivalent to a pressure of $3.25\times10^{-9}$ bar of ethanol, the signal associated with acetone was on the order of $\sim1\times10^{12}$ molecules cm$^{-2}$ s$^{-1}$ and near the noise level. Rates for bimolecular coupling on the surface are more likely to be observed at higher ethanol pressure ranges, as there is an increased probability for surface intermediates to encounter each other. Accordingly, near ambient pressure experiments were subsequently performed using the same single crystal sample.

Figure 7:
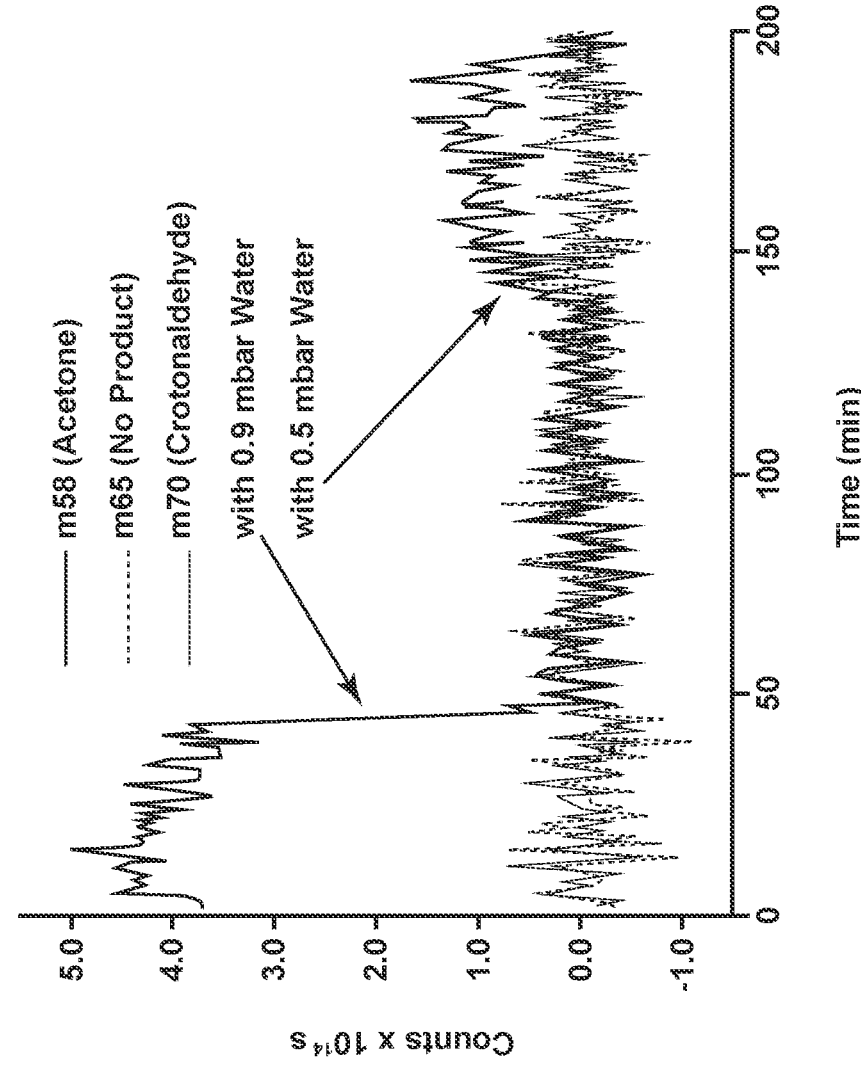
FIG. 7 is a graph of signals associated with acetone (m58), no expected product (m65), and crotonaldehyde (m70) with continuous exposure of 0.1 Torr ethanol, along with water exposure at 0.9 Torr water as well as 0.5 Torr water, over a $La_{0.7}Sr_{0.3}MnO_{3-x}(100)$ single crystal sample.

For near ambient pressure experiments, the single crystal sample was brought to elevated temperatures and continuously exposed to an ethanol partial pressure 0.1 mbar, with either an absence or an excess of water. The gas phase products were monitored using mass spectrometry via a differential pumping stage. The surface was characterized in situ by x-ray photoelectron spectroscopy (XPS). The near ambient pressure instrument: experiments were performed at 673 K and 773 K. Signals associated with acetone were seen by mass spectrometry. FIG. 7 shows the signals associated with acetone (m58), no expected product (m65), and crotonaldehyde (m70) for the experiment at 773 K in the presence of water, with continuous exposure of 0.1 Torr ethanol, along with water exposure at 0.9 Torr water as well as 0.5 Torr water, over $La_{0.7}Sr_{0.3}MnO_{3-x}(100)$. The signal at m65 serves as a blank. It is evident that crotonaldehyde is not detected while there is acetone production. The complete product steady state partial pressures and uncertainties ($1\sigma$) are shown in the table found in FIG. 8. It can be seen that catalytic acetone formation over $La_{0.7}Sr_{0.3}MnO_{3-x}(100)$ is promoted by the presence of water, which was the same observation in the powder experiments.

During the near ambient pressure experiments, in situ x-ray photoelectron spectroscopy was performed. For $La_{0.7}Sr_{0.3}MnO_{3-x}(100)$, the Mn 2p 3/2 peak shifts to lower binding energy when the surface is reduced and oxygen vacancies are created. FIG. 9 shows the XPS Mn 2p 3/2 peak scans acquired with freshly oxidized $La_{0.7}Sr_{0.3}MnO_{3-x}(100)$ on the surface (bottom trace in graph)), as well as under 0.1 mbar ethanol (middle trace in graph), and under 0.1 mbar ethanol+0.9 mbar $H_2O$ (top trace in graph). The shift to lower wavenumbers compared to the oxidized sample that is observed in the two upper traces is indicative of a chemically reduced surface. Thus, it was observed that even under conditions with a continuous exposure of excess water that the sample remained in a reduced state at 773 K. Surface oxygen vacancies can provide crucial strongly binding sites for longer-lived intermediates, and can be involved in bimolecular coupling reactions at such elevated temperatures. The observation that the $La_{0.7}Sr_{0.3}MnO_{3-x}(100)$ surface remained reduced even under an excess of water is likely an important factor for the performance of this catalyst system.

Experiments were also performed with isotopically labelled ethanol, $CD_3CH_2OH$, as this can provide useful data for gaining insight into the coupling mechanism. The same reaction conditions were used as in connection with FIG. 1 above. The trends for the production of the various isotopomers of acetone and crotonldehdye are shown in FIG. 10 (partial pressures of isotopically labelled acetone in the effluent for $CD_3CH_2OH$ conversion over $La_{0.7}Sr_{0.3}MnO_{3-x}$ powder with 1 Torr of $CD_3CH_2OH$ and 9 Torr of $H_2O$) and FIG. 11 (partial pressures of isotopically labelled crotonaldehyde in the effluent for $CD_3CH_2OH$ conversion over $La_{0.7}Sr_{0.3}MnO_{3-x}$ powder with 1 Torr of $CD_3CH_2OH$ and 9 Torr of $H_2O$).

The complete set of products of the catalytic conversion of ethanol include acetaldehyde, ethene, CO, $CO_2$, $H_2$, $H_2O$, acetone, and crotonaldehyde. The oxygen vacancy formation over $La_{0.7}Sr_{0.3}MnO_{3-x}(100)$ pushes the selectivity towards the C2 products (ethene and acetaldehyde). Further, the single oxygen vacancies produce ethene, and increasing extents of surface reduction increase acetaldehyde formation to greater extents due to paired oxygen vacancies. It thus follows that addition of an oxidant to replenishment of surface oxygens, such as $H_2O$, may be necessary to push the reaction selectivity towards C3 and C4 products. As will be discussed below, feeding of $H_2O$ also changes the selectivity between C3 and C4 products.

Various mechanisms have been proposed in the literature for crotonaldehyde and acetone formation, as summarized below. In mechanisms for crotonaldehyde formation, it is typically proposed that acetaldehyde is formed (from ethanol) followed by an aldol addition reaction. There are several variations of aldol addition on reducible oxides, which can occur either in the absence or in the presence of oxygen vacancies. Thus far, low temperature crotonaldehyde formation (<500 K) has been observed in the absence of oxygen vacancies metal oxides, while high temperature crotonaldehyde formation mechanisms (>500 K) have been observed in the presence of oxygen vacancies. Based on crotonaldehyde only being observed at temperatures >500 K and with a very small (<1%) yield, we infer that the crotonaldehyde formation occurs by aldol addition with one vacancy or with a pair of vacancies. Mechanisms for acetone formation generally involve a C4 intermediate formed by C—C coupling, followed by $CO/CO_2$ elimination at a later step. Such proposed mechanisms explain why $CO_2$ is a common accompanying product to acetone formation, as observed herein. Acetone formation has been observed during steam reforming conditions and similar temperature ranges over $La_{0.6}Sr_{0.4}Co_{1-y}Fe_yO_3$, $CuO/CeO_2$, and promoted iron oxide catalysts ($CaO/Fe_2O_3$, $ZnO/Fe_2O_3$, $MnO/Fe_2O_3$), $ZnO$, $ZrO_2$, $Zn_xZr_yO_z$, $Ga_2O_3$—$ZrO_2$, and $Sc/In_2O_3$. Among these studies, there have been proposals that acetone formation occurred by aldol addition (C—C coupling between aldehydes/enolates) as well as proposals that acetone formation could occur by direct ketonization (C—C coupling between acetates/acyl species). It has been shown for some catalysts that when starting with acetic acid as a reactant, that acetates/acyl groups couple to a beta-keto acetate intermediate, which then loses $CO_2$ to create acetone. For this system, $La_{0.7}Sr_{0.3}MnO_{3-x}(100)$ and >500K, alkoxy species and aldehydes have short residence times unless they are in oxygen vacancies. Also, acetate species will rapidly decompose to ketene and combustion type products. For example, a computational study for ethanol to acetaldehyde to acetone over $In_2O_3$ found that the largest barrier in the aldol coupling type pathway was more favorable than the largest barrier in the direct ketonization pathway.

As shown herein, crotonaldehyde was detected and appeared to be in competition with acetone formation, with the selectivity between these pathways modulated by the presence of water, as shown in FIG. 12 (partial pressures of acetone and crotonaldehyde in the effluent for ethanol conversion over $La_{0.7}Sr_{0.3}MnO_{3-x}$ powder in the absence of water and in the presence of an excess of water. The data is from the same experiments as shown in FIGS. 3-6 above, with 1 Torr of ethanol in the feed. The crotonaldehyde formation is shown on a different scale so that the trends can be better compared. The relative scale of crotonaldehyde production is shown by the expansion lines between the two graphs. Acetone production is enhanced by the presence of water while crotonaldehyde production is suppressed by the presence of water). It was observed that acetone production is enhanced by the presence of water while crotonaldehyde production is suppressed by the presence of water. Some studies have proposed that lattice oxygen is involved in this phenomenon and that one of the roles of water is to replenish the oxygen vacancies. We agree with the interpretation that one of the roles of water is to replenish oxygen vacancies. If replenishing oxygen vacancies were the only role of water, we would anticipate that feeding $O_2$ would also promote acetone formation. However, we are not aware of any study showing that $O_2$ promotes acetone formation from ethanol over reducible oxides in a way that is comparable to the promotion by water. The equilibrium between the intermediate and the oxygen-vacancy-bound alpha-beta unsaturated carbonyl species involves an OH species, and the presence of water would shift this equilibrium towards acetone. This equilibrium provides a second role for water and helps to explain why the effect of water is greater than first order (since water is involved in both vacancy replenishment and shifting the equilibrium).

The initial C—C formation could in principle occur by paired vacancies or single vacancies, followed by the presence of water pushing the system towards acetone formation. However, we believe that paired vacancies are not likely to be present in large quantities in this temperature range. As shown in FIGS. 3-6, the presence of 9 Torr of water essentially completely suppresses the acetaldehyde route, which is consistent with removing paired vacancies. This suggests that aldol addition by single vacancy is the dominant pathway. Further evidence for this pathway comes from the isotopic labeling experiments (FIGS. 10 and 11). Of the originally labelled methyl carbons, the amount of deuterium expected to be retained for crotonaldehyde and acetone formation for each path are as follows: paired vacancies will retain 4 for crotonaldehyde and 4 for acetone or 3 for crotonaldehyde and 3 for acetone, while the single vacancy pathway will retain 4 for crotonaldehyde and 5 for acetone. In all cases, the amount of deuterium will further decrease from subsequent exchange with the excess of unlabeled hydrogen present on the surface. For both C—C coupling products, the highest quantities of deuterium retainment were observed (4 for crotonaldehyde and 5 for acetone), consistent with the single vacancy pathway.

Turnover frequencies (TOFs) for acetone formation were calculated for the atmospheric powder flow experiments and for the ultra high vacuum continuous exposure experiments described above, based on the surface area of the catalyst and the number of sites per area ($1.04 \times 10^{19}$ surface cations per $m^2$). The calculated turnover frequencies are shown in FIG. 13 for ethanol:water ratios of 1:9 in the two respective types of experiments (ethanol conversion over $La_{0.7}Sr_{0.3}MnO_{3-x}$ powder and $La_{0.7}Sr_{0.3}MnO_{3-x}(100)$ single crystal sample in presence of water), along with TOFs obtained under qualitatively similar conditions over ZnO, Co—$ZrO_2$, Co—$CeO_2$—$ZrO_2$, and Co—$CeO_2$ as comparative examples. FIG. 13 also shows an upper limit for an elementary step rate based on a pre-exponential of $10^{13}$ s$^{-1}$ with an activation energy of 1.37 eV. The TOFs obtained at 1 Torr of ethanol over the $La_{0.7}Sr_{0.3}MnO_{3-x}$ powders are remarkably close to the TOFs obtained at $3.25 \times 10^{-9}$ bar for the $La_{0.7}Sr_{0.3}MnO_{3-x}(100)$ single crystal sample. The dashed line with open circles corresponds to 1 Torr of ethanol over the $La_{0.7}Sr_{0.3}MnO_{3-x}$ powders while the solid line with filled circles corresponds to $3.25 \times 10^{-9}$ bar of ethanol over the $La_{0.7}Sr_{0.3}MnO_{3-x}(100)$ single crystal sample. The larger dashed line at the top of the graph shows an upper limit for the calculated barrier of 1.37 eV for acetone production. Open squares show TOFs over ZnO measured with 18 Torr of ethanol and an ethanol:water ratio of 1:9. Open triangles show TOFs over Co/$ZrO_2$, Co/$CeO_2$—$ZrO_2$, and Co/$CeO_2$. It can be seen that the experimentally calculated TOFs for $La_{0.7}Sr_{0.3}MnO_{3-x}(100)$ are realistic in magnitude and similar to those obtained over ZnO, though a higher selectivity towards acetone was achieved in this study over $La_{0.7}Sr_{0.3}MnO_{3-x}(100)$. Over Co—$ZrO_2$, one study reported that 90% of the carbon goes through acetone, with selectivity in excess of 50% towards acetone achieved under comparable ethanol to water ratios (1:10), with 54 Torr of ethanol and 723 K. However, the systems with Co supported particles deactivate as a result of carbon deposition. The data collected herein with $La_{0.7}Sr_{0.3}MnO_{3-x}$ has not involved cation tuning, optimization of conditions, or the addition of metallic particles. Given the activity and selectivity observed for conversion of ethanol to acetone, $La_{0.7}Sr_{0.3}MnO_{3-x}$ and related perovskite systems with other A and B cations (such as Ca, Fe, Co, etc.) may provide for selective and tunable ethanol conversion.

In conclusion, catalytic conversion of ethanol in the presence and absence of co-fed water was investigated over $La_{0.7}Sr_{0.3}MnO_{3-x}$ powder and also a single crystal sample with $La_{0.7}Sr_{0.3}MnO_{3-x}(100)$ termination. The products detected were ethene, acetaldehyde, acetone, crotonaldehyde, CO, $CO_2$, and $H_2$, with particularly high conversion to acetone in the presence of co-fed $H_2O$. Based on experimental observations, a new aldol addition route to acetone is proposed through an intermediate.

The presence of $H_2O$ shifted the selectivity towards acetone over both $La_{0.7}Sr_{0.3}MnO_{3-x}$ powder and also the single crystal sample with $La_{0.7}Sr_{0.3}MnO_{3-x}(100)$ termination. Isotopic labeling experiments were used to gain insight into the C—C coupling reaction mechanism to C3 and C4 products. The data were consistent with a pathway involving acetaldehyde species and surface oxygen vacancies, and consistent with a common intermediate leading to both crotonaldehyde and acetone formation. Based on this observation, a new pathway and previously unreported C4 transition state was hypothesized. The observed turnover frequencies over both the $La_{0.7}Sr_{0.3}MnO_{3-x}$ powder and also the $La_{0.7}Sr_{0.3}MnO_{3-x}(100)$ single crystal are remarkably close to each other and of a realistic magnitude when compared to what might be expected based on the proposed new pathway. The activity is also in line with what has been observed over other reducible oxides where aldol addition to acetone was postulated to play a role.

The proposed pathway and mechanistic network provides two roles for $H_2O$. $H_2O$ may play dual roles of 1) shifting the C4 intermediate's equilibrium towards acetone formation, and 2) filling oxygen vacancies to prevent over-reduction of the surface. It has already been shown that when the surface is very reduced that the surface catalyzes conversion of ethanol towards acetaldehyde and ethene. Two roles for $H_2O$ in the promotion of acetone formation is also consistent with greater than first order $H_2O$ dependence.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A method of ethanol conversion to higher carbon compounds, the method comprising:

feeding a reactant to a reactor, wherein the reactant includes ethanol;

introducing the reactant to a perovskite catalyst in the reactor;

wherein the perovskite catalyst promotes the formation of the higher carbon compounds from ethanol.

2. The method of claim 1, wherein the perovskite catalyst has the formula $ABO_3$, wherein A is one or more selected from a group consisting of La and Sr, and wherein B is one or more selected from a group consisting of Mn, Ca, Fe, and Co.

3. The method of claim 1, wherein the perovskite catalyst is $La_{0.7}Sr_{0.3}MnO_3$.

4. The method of claim 1, wherein the reactant further includes water.

5. The method of claim 4, wherein the water is in the form of steam.

6. The method of claim 1, wherein the reactant does not include water.

7. The method of claim 1, wherein the temperature in the reactor is in the range of 300 K to 800 K.

8. The method of claim 1, wherein the pressure in the reactor is at atmospheric pressure.

9. The method of claim 1, wherein the pressure in the reactor is below atmospheric pressure.

10. The method of claim 1, wherein the perovskite catalyst is in the form of a powder or a thin film deposited on a crystal.

11. The method of claim 1, wherein the higher carbon compounds include at least one of acetone and crotonaldehyde.

12. A method of producing acetone from ethanol, the method comprising:

feeding a source of ethanol to a reactor;

feeding a source of water to the reactor;

in the reactor, introducing the ethanol and water to a catalyst including a perovskite;

wherein the perovskite catalyzes a reaction of the ethanol in the presence of water to obtain acetone.

13. The method of claim 12, wherein the perovskite is $La_{0.7}Sr_{0.3}MnO_3$.

14. The method of claim 12, wherein the water is in the form of steam.

15. The method of claim 12, wherein the ethanol is in the form of vapor.

16. The method of claim 12, wherein the temperature in the reactor is in the range of 300 K to 800 K.

17. The method of claim 12, wherein the pressure in the reactor is less than or equal to atmospheric pressure.

18. A catalyst for converting ethanol to higher carbon compounds, the catalyst comprising a perovskite having the formula $La_{0.7}Sr_{0.3}MnO_3$.

* * * * *